(12) United States Patent
Santamaria (10) Patent No.: US 11,324,810 B2
(45) Date of Patent: May 10, 2022

(54) METHOD FOR PRODUCING PEPTIDE ACE INHIBITORS

(71) Applicant: Marco Santamaria, Albuquerque, NM (US)

(72) Inventor: Marco Santamaria, Albuquerque, NM (US)

(73) Assignee: St. Marie Intellectual Property Holdings, LLC, Albuquerque, NM (US)

( * ) Notice: Subject to any disclaimer, the term of this patent is extended or adjusted under 35 U.S.C. 154(b) by 0 days.

(21) Appl. No.: 16/221,836

(22) Filed: Dec. 17, 2018

(65) Prior Publication Data

US 2019/0262436 A1   Aug. 29, 2019

Related U.S. Application Data

(60) Provisional application No. 62/634,451, filed on Feb. 23, 2018.

(51) Int. Cl.
| | |
|---|---|
| *A61K 38/55* | (2006.01) |
| *A61K 38/48* | (2006.01) |
| *C12N 9/48* | (2006.01) |
| *C12N 9/76* | (2006.01) |
| *A61P 9/12* | (2006.01) |
| *A61K 38/08* | (2019.01) |
| *A23L 29/00* | (2016.01) |
| *C12N 9/64* | (2006.01) |

(52) U.S. Cl.
CPC .......... *A61K 38/4826* (2013.01); *A23L 29/06* (2016.08); *A61K 38/085* (2013.01); *A61K 38/486* (2013.01); *A61P 9/12* (2018.01); *C12N 9/485* (2013.01); *C12N 9/6427* (2013.01); *C12N 9/6448* (2013.01)

(58) Field of Classification Search
None
See application file for complete search history.

(56) References Cited

U.S. PATENT DOCUMENTS

| | | | |
|---|---|---|---|
| 5,369,015 A | 11/1994 | Yoshikawa et al. | |
| 8,759,295 B2 * | 6/2014 | Ghosh | A61P 9/04 514/16.2 |
| 2006/0073543 A1 | 4/2006 | Gowda et al. | |
| 2010/0093640 A1 | 4/2010 | Bonte et al. | |

FOREIGN PATENT DOCUMENTS

| | | | |
|---|---|---|---|
| GB | 2020832 A | | 4/1979 |
| JP | 11060596 A | * | 3/1999 |
| WO | WO2001/093712 | | 12/2001 |
| WO | WO2006/052260 | | 5/2006 |

OTHER PUBLICATIONS

Huang, Journal of Food and Drug Analysis. vol. 18. No. 6. 2010, pp. 458-463 (Year: 2010).*
Aldred, Biofouling vol. 24, No. 2, Jan. 2008, 97-107 (Year: 2008).*
Wang, Extracts and Applications, Food Science and Technology, vol. 40, No. 05, 2015 (Year: 2015).*
Vercruysse, J. Agric. Food Chem. 2005, 53, 8106-8115 (Year: 2005).*
English Translation of JP 11060596 A, 8 pages, 1999 (Year: 1999).*
Ahmad Asoodeh et al., "Purification and charicterisation of angiotensin I converting enzyme inhibitory peptides fromm lysozyme hydrolysates", Food Chemistry, 2012, 291-295, 131.
Jiapei Wang et al., "Purification and identification of a ACE inhibitory peptide from oyster proteins hydrolysate . . . ", Food Chemistry, 2008, 302-308, 111.
Rong He et al., "Purification and hypotensive activity of rapeseed protein-derived renin . . . ", Journal of Funcitonal Foods, 2013, 781-789, 5.
Runqiang, Yang et al., "Accumulation and Identification of Angiotensin-Converting Enzyme Inhibitory Peptides . . . ", J. of Agricultural and Food Chemistry, 2011, 3598-3605,59.
Lieselot, Vercruysse et al., "ACE Inhibitory Peptides Derived from Enzymatic Hydrolystates of Animal Muscle Protein . . . ", J. of Agricultural and Food Chemistry, 2005, 1-10.

* cited by examiner

*Primary Examiner* — Satyanarayana R Gudibande
(74) *Attorney, Agent, or Firm* — Marco Henry Santamaria (57) ABSTRACT

A method for producing ACE Inhibitor peptides from a protein source or plasma is disclosed. The method utilizes proteolysis by intestinal, blood-circulating, or membrane-bound proteases. The initial synthesis step could require obtaining a protein source either from a human or animal. A protease is added to either a given plasma protein or plasma and incubated. Following incubation, the protease activity must be quenched using a protease inhibitor to inactivate the protease. After incubation with protease inhibitor, the solution will contain a mixture of bioactive ACE inhibitory peptides and inert peptides. This mixture may be purified to select for the ACE inhibitory peptides through centrifugation. The mixture may also be sterilized to remove any microbial contaminants. The ACE inhibitory peptides can be mixed with protein powders, incorporated into baked good and put into other food products to provide food products with the added benefit of lowering blood pressure.

11 Claims, 8 Drawing Sheets

METHOD FOR PRODUCING PEPTIDE ACE INHIBITORS

CROSS-REFERENCE TO PROVISIONAL APPLICATION

This application claims priority under 35 U.S.C. 119(e) to U.S. Provisional Patent Application Ser. No. 62/634,451, entitled "METHOD FOR PRODUCING PEPTIDE ACE INHIBITORS FROM PLASMA AND PROTEIN SOURCES," which was filed on Feb. 23, 2018, the disclosure of which is incorporated herein by reference in its entirety.

TECHNICAL FIELD

Embodiments are generally related to peptide angiotensin-converting enzyme (ACE) inhibitors. Embodiments are additionally related to a method for producing peptide ACE inhibitors. Embodiments also relate to producing peptide ACE inhibitors from plasma and protein sources.

BACKGROUND

Hypertension is a condition afflicting millions of people per year. It is a co-morbidity related to diabetes, atherosclerosis and a host of other conditions. Hypertension results when angiotensin II causes the muscles surrounding blood vessels to contract and narrow the vessels. Blood pressure increases when the vessels narrow.

A typical treatment for hypertension is angiotensin converting enzyme (ACE) inhibitors to maintain lower blood pressure. ACE inhibitors function by inhibiting the enzyme that converts angiotensin I to angiotensin II. Angiotensin converting enzyme conversion of angiotensin I to angiotensin II physiologically results in vasoconstriction of the blood vessels, causes an increase in blood pressure, and often results in kidney disease. ACE inhibitors help to prevent this type of kidney disease by reducing intraglomerular pressure caused by release of angiotensin II.

Previous studies show that ACE inhibitors have limitations in terms of how effective they can be in inhibiting the functionality of the renin-angiotensin-aldosterone system (RAAS). The renin-angiotensin system, working together with the kidneys, is the body's most important long-term blood pressure regulation system. This can result in a decreased state of health for patients as well as money spent by the patient on drugs that do not fully achieve their designed purpose. In addition, methods used to produce ACE inhibitors have historically been costly and time-intensive.

Accordingly, the composition and method disclosed herein is intended to solve such problems such that peptide ACE inhibitors for reducing blood pressure are produced from plasma and protein sources in a cost efficient manner.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, an aspect of the disclosed embodiments to provide enhanced peptide angiotensin-converting enzyme (ACE) inhibitors.

It is another aspect of the invention to provide a method for producing peptide ACE inhibitors.

It is yet another aspect of the disclosed invention to produce peptide ACE inhibitors from plasma and protein sources.

The aforementioned aspects and other objectives and advantages can now be achieved as described herein. A method for producing ACE Inhibitor peptides from a protein source or plasma is disclosed. The method utilizes proteolysis by intestinal, blood-circulating, or membrane-bound proteases. The initial synthesis step could require obtaining a protein source either from a human or animal. A protease is added to either a given plasma protein or plasma and incubated. Following incubation, the protease activity must be quenched using a protease inhibitor to inactivate the protease. After incubation with protease inhibitor, the solution will contain a mixture of bioactive ACE inhibitory peptides and inert peptides. This mixture may be purified to select for the ACE inhibitory peptides through centrifugation. The mixture may also be sterilized to remove any microbial contaminants. The ACE inhibitory peptides can be mixed with protein powders, incorporated into baked good and put into other food products to provide food products with the added benefit of lowering blood pressure.

In an embodiment, a method of making polypeptide angiotensin converting enzyme (ACE) inhibitors from plasma proteins is disclosed. In certain embodiments, the method can comprise mixing a protein source with at least one protease; quenching the at least one protease mixed with the protein source to create the polypeptide angiotensin converting enzyme (ACE) inhibitors; and inhibiting the at least one protease mixed with the protein source completely with the polypeptide angiotensin converting enzyme (ACE) inhibitors.

In another embodiment, the protein source is mixed with the at least one protease for up to 24 hours at up to 40 degrees Celsius. In an embodiment, the protein source is selected from at least one of serum albumin and macroglobulin. In yet another embodiment, the protein source is at a concentration up to a saturation point of the protein source. In another embodiment, the at least one protease is selected at least one of trypsin, chymotrypsin, and elastase. In some embodiments, the at least one protease is at a concentration up to one tenth of a concentration of a plasma protein. In yet another embodiment, quenching comprises removing protease activity by any chemical or mechanical means comprising at least one of filtration, boiling, or utilizing a protease inhibitor, wherein the protease inhibitor is at a concentration up to one tenth of a concentration of the at least one protease. In certain embodiments, the method can further comprise incorporating the polypeptide angiotensin converting enzyme (ACE) inhibitors into food products, wherein the food products can comprise at least one of protein powder and a baked good and a user consuming the food products containing the polypeptide angiotensin converting enzyme (ACE) inhibitors to lower the blood pressure of the user.

In another embodiment, a method of making polypeptide angiotensin converting enzyme (ACE) inhibitors from plasma proteins is disclosed. In certain embodiments, the method can comprise: mixing plasma with at least one protease; quenching the at least one protease mixed with the plasma to create the polypeptide angiotensin converting enzyme (ACE) inhibitors; and inhibiting the at least one protease mixed with the plasma completely with the polypeptide angiotensin converting enzyme (ACE) inhibitors.

In some embodiments, the plasma is mixed with the at least one protease for up to 24 hours at up to 40 degrees Celsius. In other embodiments, the at least one protease is selected from at least one of trypsin, chymotrypsin, and elastase. In yet another embodiment, the at least one protease is at a concentration up to 1 g/mL. In an embodiment, quenching comprises removing protease activity by any chemical or mechanical means comprising at least one of filtration, boiling, or utilizing a protease inhibitor, wherein the protease inhibitor is at a concentration up to one tenth of a concentration of the at least one protease. In yet another embodiment, the method can further comprise incorporating the polypeptide angiotensin converting enzyme (ACE) inhibitors into food products, wherein the food products can comprise at least one of protein powder and a baked good and a user consuming the food products containing the polypeptide angiotensin converting enzyme (ACE) inhibitors to lower the blood pressure of the user.

In another embodiment, a method of making polypeptide angiotensin converting enzyme (ACE) inhibitors from plasma proteins is disclosed. In some embodiments, the method can comprise: mixing plasma with at least one protease, wherein the at least one protease comprises chymotrypsin; quenching the at least one protease with the mixed plasma and chymotrypsin to create the polypeptide angiotensin converting enzyme (ACE) inhibitors; and inhibiting chymotrypsin mixed with the plasma completely with the polypeptide angiotensin converting enzyme (ACE) inhibitors.

In certain embodiments, the plasma is mixed with chymotrypsin for up to 24 hours at up to 40 degrees Celsius. In other embodiments, chymotrypsin is at a concentration up to 1 g/mL. In yet another embodiment, quenching comprises removing protease activity by any chemical or mechanical means comprising at least one of filtration, boiling, or utilizing a protease inhibitor, wherein the protease inhibitor is at a concentration up to one tenth of a concentration of chymotrypsin. In some embodiments, the method can further comprise incorporating the polypeptide angiotensin converting enzyme (ACE) inhibitors into food products, wherein the food products can comprise at least one of protein powder and a baked good and a user consuming the food products containing the polypeptide angiotensin converting enzyme (ACE) inhibitors to lower the blood pressure of the user.

BRIEF DESCRIPTION OF THE FIGURES

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof (other than software per se). The following detailed description is, therefore, not intended to be interpreted in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood, at least in part, from usage in context. For example, terms such as "and", "or", or "and/or" as used herein may include a variety of meanings that may depend, at least in part, upon the context in which such terms are used. Typically, "or" if used to associate a list, such as A, B, or C, is intended to mean A, B, and C, here used in the inclusive sense, as well as A, B, or C, here used in the exclusive sense. In addition, the term one or more as used herein, depending at least in part upon context, may be used to describe any feature, structure, or characteristic in a singular sense or may be used to describe combinations of features, structures, or characteristics in a plural sense. Similarly, terms such as "a", "an", or "the", again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

In certain embodiments, a method for producing ACE Inhibitor peptides from a protein source or plasma is disclosed. The disclosed embodiments use either a purified protein or plasma as a substrate to generate peptides. Plasma is a low-cost alternative to using purified proteins as plasma may be obtained from animals with minimal expense.

The disclosed method utilizes proteolysis by intestinal, blood-circulating, or membrane-bound proteases. During physiological shock stemming from sepsis, hemorrhage, peritonitis, or other trauma, hypervolemia is experienced by the patient. The patient's body responds to this state of hypervolemia and decreased blood pressure by pulling in fluid from the patient's organs and other tissues. This causes the organs to become ischemic, with nutrient and oxygen flow to these organs becoming impaired. Given the size of the small and large intestine, a significant fraction of fluid shunted to the cardiovascular system is taken from this organ. The ischemia within the intestine results in a breakdown of the mucosal barrier lining the lumen of the intestine, allowing the luminal contents to exit the intestine and enter circulation.

Among the biological components leaving the intestine are proteases required for the digestion of food. These proteases include, but are not limited to, trypsin, chymotrypsin, and elastase. Once in the cardiovascular system, these proteases proceed to act upon circulating blood proteins, causing these blood proteins to be broken apart into peptide fragments. Given that these peptides have ACE inhibitory properties resulting in the lowering of blood pressure, it would be advantageous to be able to synthesize these peptides for use as an ACE inhibitor.

Figure 1:
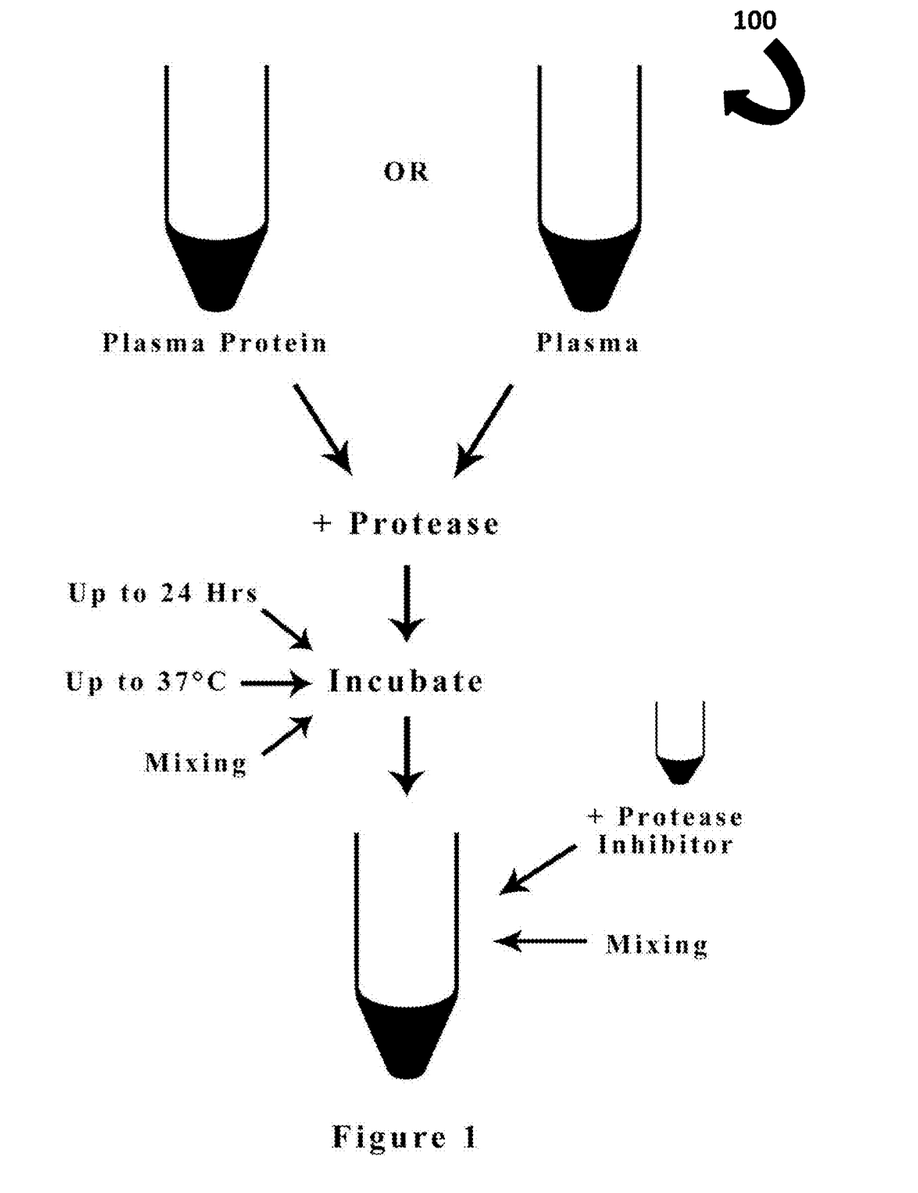
FIG. 1 illustrates a schematic of the ACE inhibitor production method, which can be implemented in accordance with an example embodiment.

FIG. 1 illustrates a schematic 100 of the ACE inhibitor production method, which can be implemented in an exemplary embodiment. In certain embodiments, the initial synthesis step could require obtaining a protein source. This protein would preferably be of human origin to maximize the homology between the protein being used and the patient receiving the peptide fragments, however proteins from animal origins can be used in additional embodiments. A protease is added to either a given plasma protein or plasma and incubated preferably for up to 24 hours at up to 37 degrees Celsius preferably and mixed throughout the incubation. Protease inhibitor is then mixed in to inactivate the protease.

With regard to albumin, the albumin may be of bovine or chicken origin, being derived from either blood serum or eggs. The purity of the protein should be at least 80% to ensure that sufficient substrate is available for action by the proteases. The proteases incubated with the protein source may be any of those located in the lumen of the intestine, in the cardiovascular circulation, or attached to cell membranes but trypsin, chymotrypsin, or elastase would be preferred. Each protease or combination or proteases may be incubated for up to 24 hours with the protein source, with lower incubations needed for optimized substrate to protease ratios. During incubation the incubation mixture should be stirred, or otherwise perturbed, to facilitate the reaction and the temperature may be up to 40 degrees Celsius and should preferably be at 37 degrees Celsius to increase and optimize the rate of reaction kinetics.

In certain embodiments, the concentration of proteases may be up to the saturation point of the solvent. Preferable concentrations of plasma protein should be in the grams per deciliter range. The solvent itself may be, but is not limited to, normal saline, phosphate buffered saline, or any buffered solution. The concentration of proteases may be calculated using a ratio relative to the concentration of the plasma protein. The ratio may vary, but preferably should be between 1:10,0000 and 1:100 protease concentration to plasma protein concentration. Both the plasma protein and protease should be fully soluble in the solvent.

Following incubation, the protease activity must be quenched using a protease inhibitor. "Quenching" refers to removing protease activity by any chemical or mechanical means including, but not limited to, filtration, boiling or protease inhibitor. While the amount of protease inhibitor used may be up to one tenth of the amount of protease used, it is preferable for the protease inhibitor to be in a ratio relative to protease of between 1:10,0000 protease inhibitor to protease to 1:100 protease inhibitor to protease. The protease inhibitor should be mixed by stirring, or otherwise perturbing, the solution for up to 24 hours.

After incubation with protease inhibitor, the solution will contain a mixture of bioactive ACE inhibitory peptides and inert peptides. This mixture may be purified to select for the ACE inhibitory peptides through centrifugation that separates the 10 kDa peptides from the remaining peptides. Either following this step or following the quenching of the proteases by proteases inhibitors, the mixture may also be sterilized to remove any microbial contaminants.

EXPERIMENTAL DATA

In Vitro Experiments

FIGS. 2 through 8 illustrate in vitro ACE inhibition in accordance with exemplary embodiments. Albumin was incubated with either trypsin (a protease) or chymotrypsin (a protease) or a combination of trypsin and chymotrypsin then the protease or protease was inhibited with a protease inhibitor (PI) in a solvent of Phosphate Buffer Saline (PBS). The assay use is specifically designed to chemically test for ACE inhibition. The Assay used was the Angiotensin-Converting Enzyme (ACE) Inhibition Assay from Dojindo Molecular Technologies, Inc™.

Figure 2:
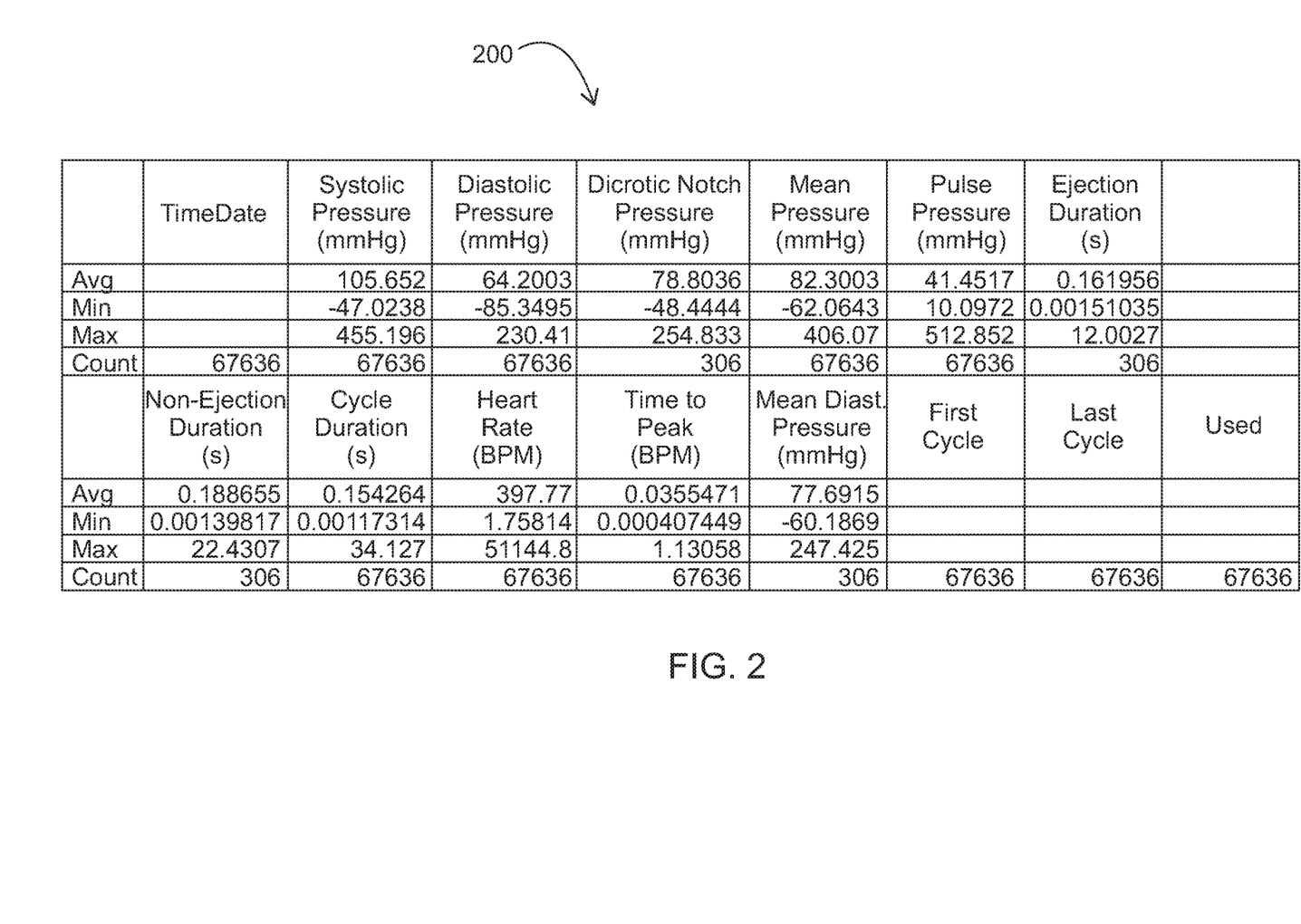
FIG. 2 illustrates a chart of the average values of animal blood pressure following femoral vein and artery cannulation, in accordance with an embodiment.
Figure 3:
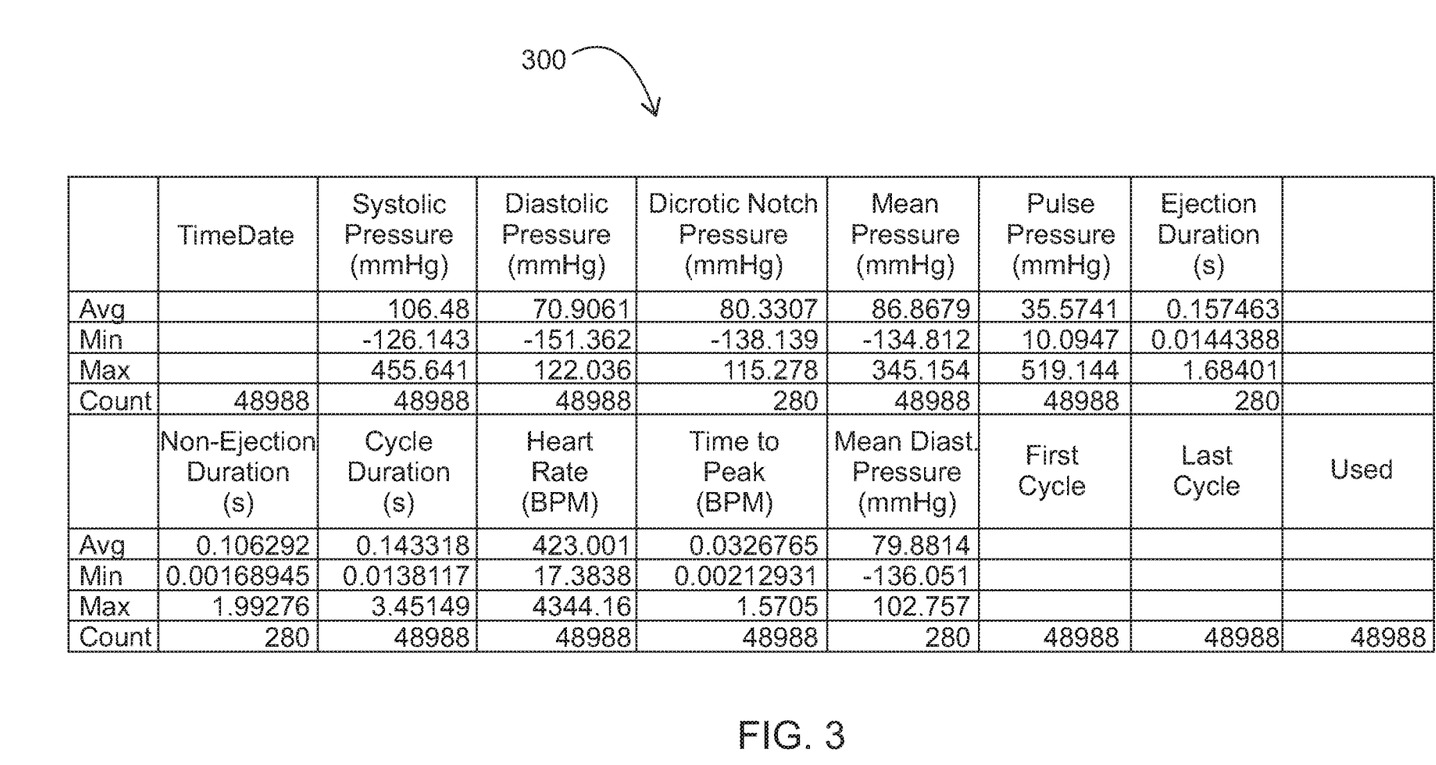
FIG. 3 illustrates a chart of the average values of animal blood pressure following femoral vein and artery cannulation, in accordance with an embodiment.

FIGS. 2 and 3 illustrate charts 200, 300 of the average values of animal blood pressure following femoral vein and artery cannulation, in accordance with an embodiment. The average values displayed are for the total course of the surgical experiment. Animal blood pressure of a rat was allowed to stabilized following femoral vein and artery cannulation for a period of at least 5 min. Subsequent to each peptide injection, animal blood pressure response was recorded via a pressure transducer. Animal blood pressure values were obtained both for a period prior to any injection and following injection effects to ensure that animal blood pressure was stable prior to each injection and before each following injection. As a result of these periods, the time span of each injection was only a fraction of the total time the animal's blood pressure was measured. This causes average blood pressure values to be higher than those values measured immediately subsequent to each injection.

Figure 4:
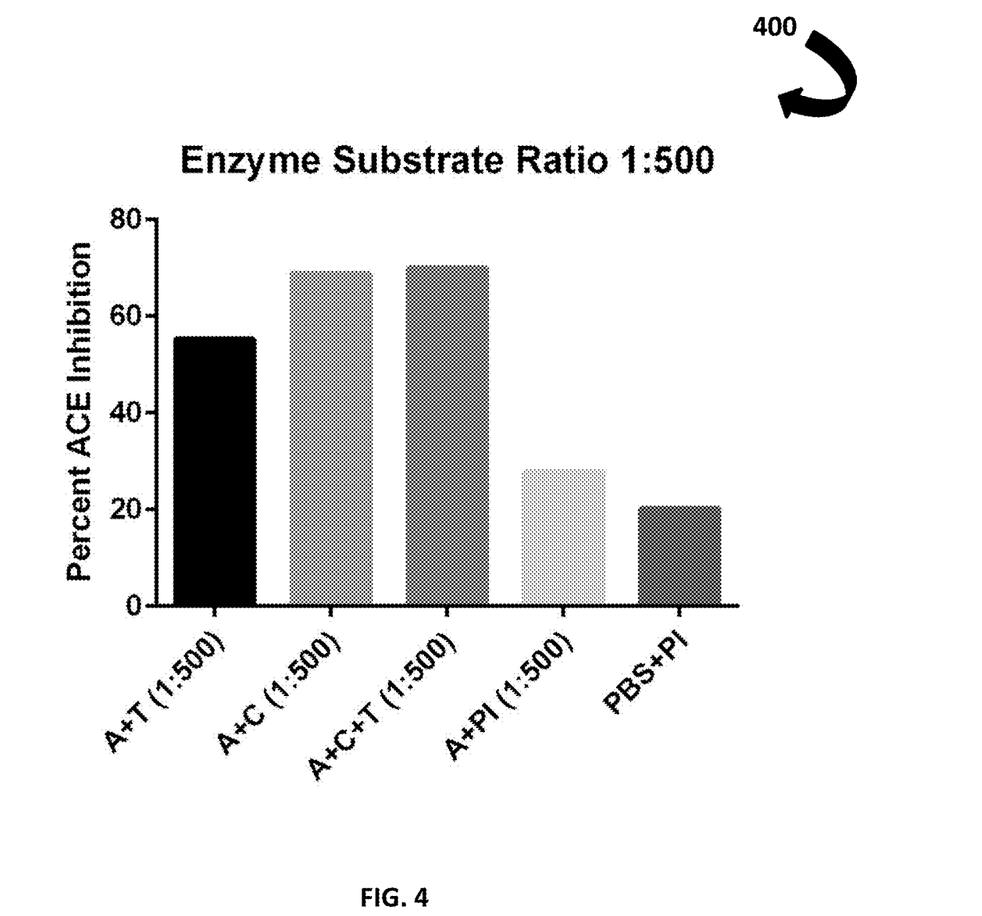
FIG. 4 illustrates a graph of concentrations of 1:500 Albumin to Protease ratio mixed with other compounds, in accordance with an embodiment, in accordance with an embodiment.

FIG. 4 illustrates a graph 400 of concentrations of 1:500 Albumin to Protease ratio mixed with other compounds, in accordance with an embodiment. The albumin concentration ratio of 1:500 Albumin+Trypsin (A+T) achieved approximately 55% ACE inhibition. Albumin+Chymotrypsin (A+C) and Albumin+Chymotrypsin+Trypsin (A+C+T) both achieved approximately 70% ACE inhibition. The control of Albumin+Protease Inhibitor (A+PI) yielded approximately 30% inhibition.

Figure 5:
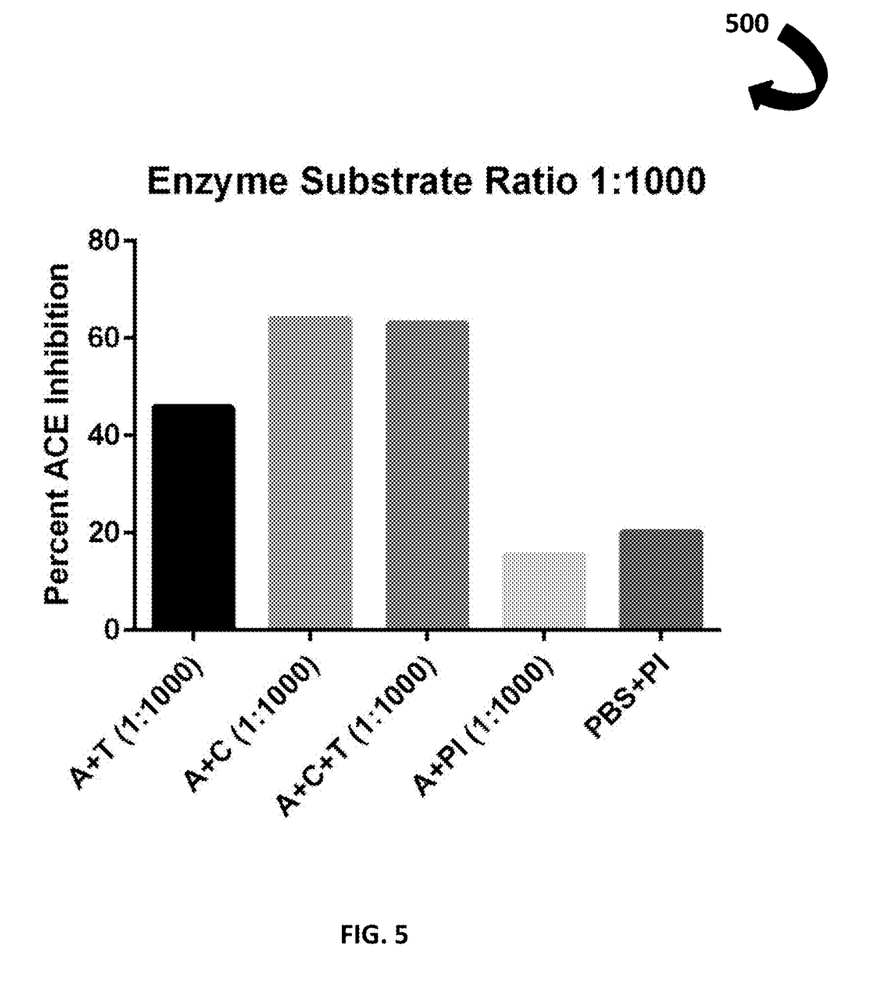
FIG. 5 illustrates a graph of concentrations of 1:1000 Albumin to Protease ratio mixed with other compounds, in accordance with an embodiment, in accordance with an embodiment.

FIG. 5 illustrates a graph 500 of concentrations of 1:1000 Albumin to Protease ratio mixed with other compounds, in accordance with an embodiment. At an albumin to protease ratio of 1:1000, Albumin+Trypsin (A+T) achieved approximately 45% ACE inhibition. Albumin+Chymotrypsin (A+C) and Albumin+Chymotrypsin+Trypsin (A+C+T) both achieved approximately 65% ACE inhibition. The control of Albumin+Protease Inhibitor (A+PI) yielded approximately 15% inhibition. PBS+PI by itself yielded 20% inhibition. These results demonstrate that combining a protein source such as albumin with a protease results in a level of ACE inhibition far exceeding that of control. The ACE inhibition produced by the control is considered noise.

In Vivo Experiments

Sprague-Dawley rats were anaesthetized with isoflurane gas and their femoral arteries and veins were used to monitor mean arterial pressure and for peptide injections, respectively. The protocol for producing the peptides is as follows:

For both experiments, the concentration of albumin was 0.2 g/mL and added 1% of protease was added. 0.1 g albumin was added in 0.5 mL saline along with 1 mg of protease. The solution was stirred and incubated at 37 degrees Celcius for 30 minutes. To stop the reaction and remove the proteases, the incubated solution was centrifuged for 20 minutes in a 3 k filter column, which rendered a little more than 0.2 mL of flow-through to inject. Thus, to be consistent, 0.2 mL of each solution was injected into the rat so the blood pressure was up and stable again for the next injection.

Figure 6:
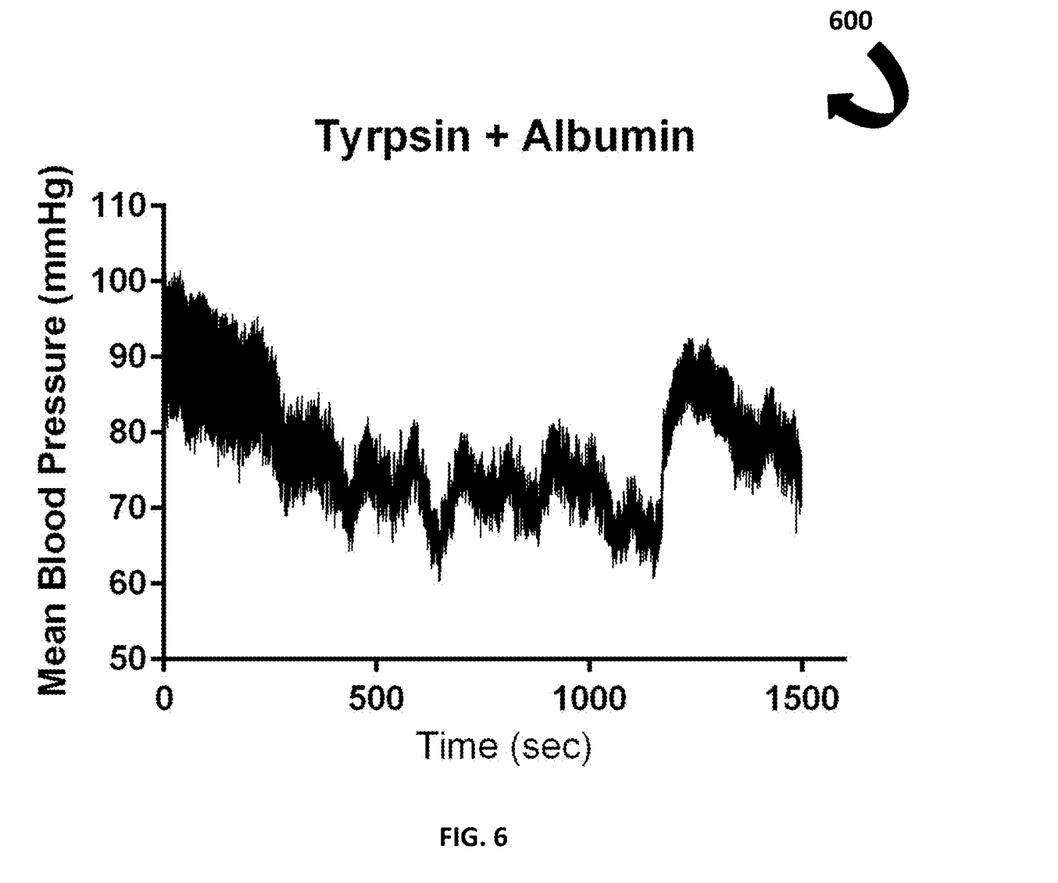
FIG. 6 illustrates a graph comparing blood pressure after injection with Trypsin and Albumin, in accordance with an embodiment.

FIG. 6 illustrates a graph 600 comparing blood pressure after injection with trypsin and albumin, in accordance with an embodiment. A rat was given a peptide injection derived from combining albumin with trypsin. In the graph 600, the blood pressure is tracing immediately following injection of the peptides. Peptides generated by combining trypsin and albumin resulted in a blood pressure decrease of approximately 30 mmHg.

Figure 7:
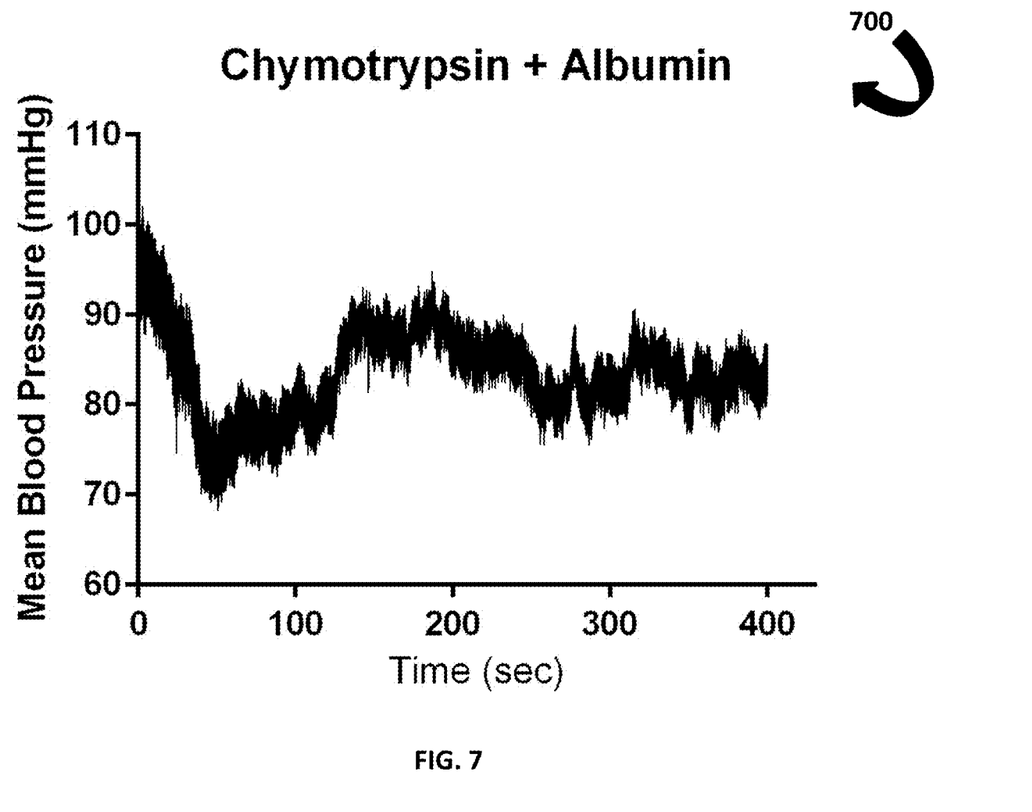
FIG. 7 illustrates a graph comparing blood pressure after injection with Chymotrypsin and Albumin, in accordance with an embodiment.

FIG. 7 illustrates a graph 700 comparing blood pressure after injection with chymotrypsin and albumin, in accordance with an embodiment. A rat was given a peptide injection derived from combining albumin with chymotrypsin. In the graph 700 the blood pressure is tracing immediately following injection of the peptides. Peptides generated by combining chymotrypsin and albumin resulted in a blood pressure decrease of 25 mmHg.

Figure 8:
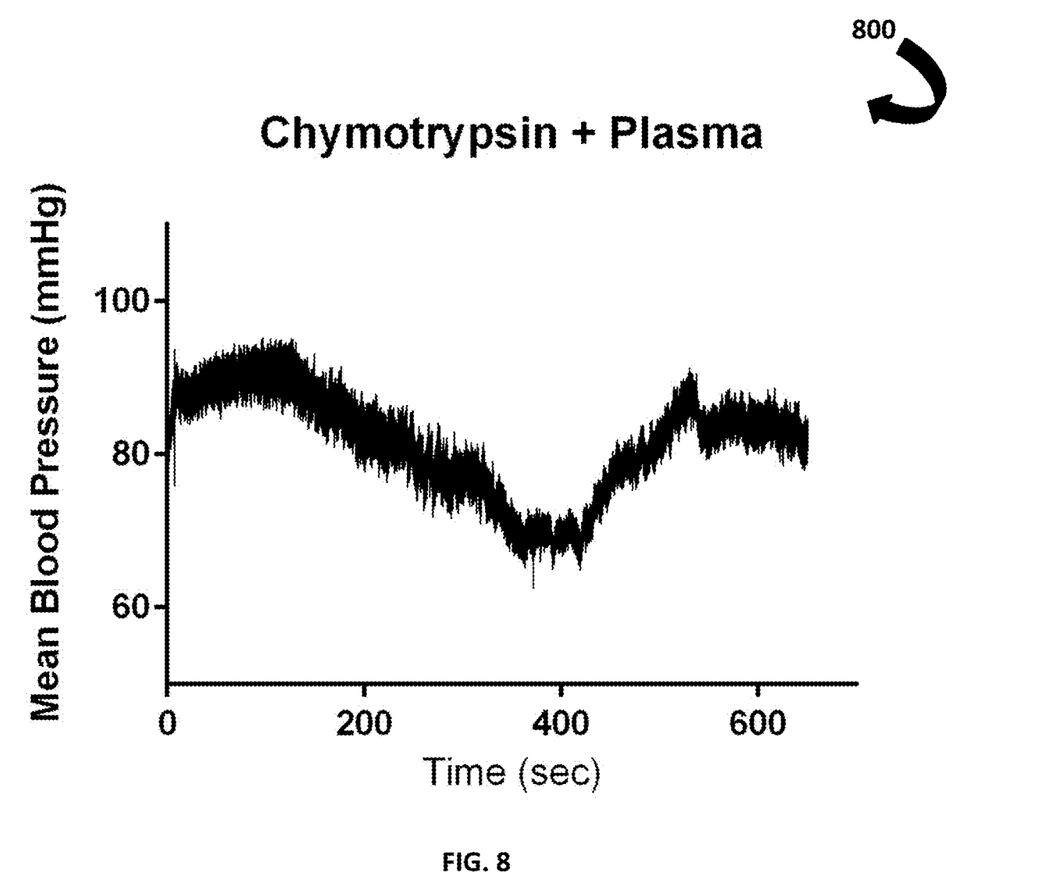
FIG. 8 illustrates a graph comparing blood pressure after injection with Chymotrypsin and Plasma, in accordance with an embodiment.

FIG. 8 illustrates a graph 800 comparing blood pressure after injection with chymotrypsin and plasma, in accordance with an embodiment. A rat was given a peptide injection derived from combining plasma with chymotrypsin. In the graph 800, the blood pressure is tracing immediately following injection of the peptides. Peptides generated by combining chymotrypsin and plasma resulted in a blood pressure decrease of 25 mmHg.

FIGS. 6-8 demonstrated a visible drop in the rat's Mean Arterial Blood Pressure (MABP) following each injection. As seen in the graphs in FIGS. 6-8, peptides generated by combining trypsin and albumin resulted in a decrease of approximately 30 mmHg, peptides generated by combining chymotrypsin and albumin resulted in a decrease of 25 mmHg, and peptides generated by combining chymotrypsin and plasma resulted in a decrease of 25 mmHg. The durations of these blood pressure decreases were 1200, 125, and 400 seconds, respectively.

Delivery methods of the disclosed polypeptide angiotensin converting enzyme (ACE) inhibitor are crucial. Normal drug delivery methods include IV and oral administration. With reference to oral administration, the peptides generated by this method are cheaply produced and highly stable and thus may be incorporated in food products. The disclosed peptide ACE inhibitor can be mixed with protein powders, incorporated into baked good and put into other food products to provide food products with the added benefit of lowering a person's blood pressure. Given that peptides are protein fragments the peptides will not adversely affect taste of food nor will they interact with food ingredients to produce detrimental effects. This assertion is supported by the current use of incorporating protein into cereals or other food products.

In an embodiment, a method of making polypeptide angiotensin converting enzyme (ACE) inhibitors from plasma proteins is disclosed. In certain embodiments, the method can comprise mixing a protein source with at least one protease; quenching the at least one protease mixed with the protein source to create the polypeptide angiotensin converting enzyme (ACE) inhibitors; and inhibiting the at least one protease mixed with the protein source completely with the polypeptide angiotensin converting enzyme (ACE) inhibitors.

In another embodiment, the protein source is mixed with the at least one protease for up to 24 hours at up to 40 degrees Celsius. In an embodiment, the protein source is selected from at least one of serum albumin and macroglobulin. In yet another embodiment, the protein source is at a concentration up to a saturation point of the protein source. In another embodiment, the at least one protease is selected at least one of trypsin, chymotrypsin, and elastase. In some embodiments, the at least one protease is at a concentration up to one tenth of a concentration of a plasma protein. In yet another embodiment, quenching comprises removing protease activity by any chemical or mechanical means comprising at least one of filtration, boiling, or utilizing a protease inhibitor, wherein the protease inhibitor is at a concentration up to one tenth of a concentration of the at least one protease. In certain embodiments, the method can further comprise incorporating the polypeptide angiotensin converting enzyme (ACE) inhibitors into food products, wherein the food products can comprise at least one of protein powder and a baked good and a user consuming the food products containing the polypeptide angiotensin converting enzyme (ACE) inhibitors to lower the blood pressure of the user.

In another embodiment, a method of making polypeptide angiotensin converting enzyme (ACE) inhibitors from plasma proteins is disclosed. In certain embodiments, the method can comprise: mixing plasma with at least one protease; quenching the at least one protease mixed with the plasma to create the polypeptide angiotensin converting enzyme (ACE) inhibitors; and inhibiting the at least one protease mixed with the plasma completely with the polypeptide angiotensin converting enzyme (ACE) inhibitors.

In some embodiments, the plasma is mixed with the at least one protease for up to 24 hours at up to 40 degrees Celsius. In other embodiments, the at least one protease is selected from at least one of trypsin, chymotrypsin, and elastase. In yet another embodiment, the at least one protease is at a concentration up to 1 g/mL. In an embodiment, quenching comprises removing protease activity by any chemical or mechanical means comprising at least one of filtration, boiling, or utilizing a protease inhibitor, wherein the protease inhibitor is at a concentration up to one tenth of a concentration of the at least one protease. In yet another embodiment, the method can further comprise incorporating the polypeptide angiotensin converting enzyme (ACE) inhibitors into food products, wherein the food products can comprise at least one of protein powder and a baked good and a user consuming the food products containing the polypeptide angiotensin converting enzyme (ACE) inhibitors to lower the blood pressure of the user.

In another embodiment, a method of making polypeptide angiotensin converting enzyme (ACE) inhibitors from plasma proteins is disclosed. In some embodiments, the method can comprise: mixing plasma with at least one protease, wherein the at least one protease comprises chymotrypsin; quenching the at least one protease with the mixed plasma and chymotrypsin to create the polypeptide angiotensin converting enzyme (ACE) inhibitors; and inhibiting chymotrypsin mixed with the plasma completely with the polypeptide angiotensin converting enzyme (ACE) inhibitors.

In certain embodiments, the plasma is mixed with chymotrypsin for up to 24 hours at up to 40 degrees Celsius. In other embodiments, chymotrypsin is at a concentration up to 1 g/mL. In yet another embodiment, quenching comprises removing protease activity by any chemical or mechanical means comprising at least one of filtration, boiling, or utilizing a protease inhibitor, wherein the protease inhibitor is at a concentration up to one tenth of a concentration of chymotrypsin. In some embodiments, the method can further comprise incorporating the polypeptide angiotensin converting enzyme (ACE) inhibitors into food products, wherein the food products can comprise at least one of protein powder and a baked good and a user consuming the food products containing the polypeptide angiotensin converting enzyme (ACE) inhibitors to lower the blood pressure of the user.

Based on the foregoing, it can be appreciated that a number of embodiments, preferred and alternative, are disclosed herein. The techniques/embodiments described herein are in no way meant to limit the breadth of potential applications. It will be appreciated that variations of the above-disclosed and other features and functions, or alternatives thereof, may be desirably combined into many other different systems or applications. Also, it can be appreciated that various presently unforeseen or unanticipated alternatives, modifications, variations or improvements therein may be subsequently made by those skilled in the art which are also intended to be encompassed by the following claims.

What is claimed is:

1. A method of making polypeptide angiotensin converting enzyme (ACE) inhibitors from plasma consisting of:
   contacting at least one serine protease with saline;
   mixing the plasma with the at least one serine protease;
   quenching the at least one serine protease mixed with the plasma.

2. The method of claim 1, wherein the plasma is mixed with at least one serine protease for between 0.1 hours to 24 hours.

3. The method of claim 1, wherein the plasma is mixed with at least one serine protease at 0° to 40° C.

4. The method of claim 1, wherein quenching comprises contacting the at least one serine protease with a protease inhibitor.

5. The method of claim 4, wherein the protease inhibitor is at a concentration of between one ten thousandth and one tenth of the concentration of the at least one serine protease.

6. The method of claim 1, wherein the plasma comprises serum albumin.

7. The method of claim 1, wherein the at least one serine protease is trypsin.

8. The method of claim 1, wherein the at least one serine protease is chymotrypsin.

9. The method of claim 1, wherein the at least one serine protease is at a concentration of between one ten thousandth and one tenth of the concentration of the plasma protein.

10. The method of claim 1, wherein the at least one serine protease is at a concentration of between 1 µg/mL and 1 g/mL.

11. The method of claim 1 further comprising:
   incorporating the polypeptide angiotensin converting enzyme (ACE) inhibitors into food product; and
   an user consuming the food products containing the polypeptide angiotensin converting enzyme (ACE) inhibitors to lower the blood pressure of the user.

* * * * *